(12) United States Patent
Lee

(10) Patent No.: US 12,408,699 B2
(45) Date of Patent: Sep. 9, 2025

(54) AEROSOL GENERATING DEVICE

(71) Applicant: KT&G CORPORATION, Daejeon (KR)

(72) Inventor: Moon Bong Lee, Seoul (KR)

(73) Assignee: KT&G CORPORATION, Daejeon (KR)

( * ) Notice: Subject to any disclaimer, the term of this patent is extended or adjusted under 35 U.S.C. 154(b) by 981 days.

(21) Appl. No.: 17/281,026

(22) PCT Filed: Dec. 9, 2020

(86) PCT No.: PCT/KR2020/017923
§ 371 (c)(1),
(2) Date: Mar. 29, 2021

(87) PCT Pub. No.: WO2021/141246
PCT Pub. Date: Jul. 15, 2021

(65) Prior Publication Data
US 2022/0400750 A1 Dec. 22, 2022

(30) Foreign Application Priority Data

Jan. 6, 2020 (KR) .................. 10-2020-0001706
Apr. 6, 2020 (KR) .................. 10-2020-0041537

(51) Int. Cl.
*A24F 40/40* (2020.01)
*A24F 40/51* (2020.01)

(52) U.S. Cl.
CPC .............. *A24F 40/40* (2020.01); *A24F 40/51* (2020.01)

(58) Field of Classification Search
CPC ......... A24F 42/00; A24F 47/00; A24C 4/3412
See application file for complete search history.

(56) References Cited

U.S. PATENT DOCUMENTS

| | | | |
|---|---|---|---|
| 4,907,607 A * | 3/1990 | Focke | ............. A24C 5/3412 131/281 |
| 4,947,874 A | 8/1990 | Brooks et al. | |
| 5,526,559 A | 6/1996 | Fleenor et al. | |
| 8,689,804 B2 | 4/2014 | Fernando et al. | |

(Continued)

FOREIGN PATENT DOCUMENTS

| | | |
|---|---|---|
| CA | 3 099 825 A1 | 11/2019 |
| CN | 1045691 A | 10/1990 |

(Continued)

OTHER PUBLICATIONS

English machine translation of CN 104010531 B; Zuber et al.; 37 pages; Jun. 4, 2019 (Year: 2019).*

(Continued)

*Primary Examiner* — Linda L Gray
(74) *Attorney, Agent, or Firm* — Sughrue Mion, PLLC

(57) ABSTRACT

An aerosol generating device includes: an accommodation portion configured to accommodate an aerosol generating article through an opening; and a deformation guiding portion that comes into contact with one end of the aerosol generating article when the aerosol generating article is inserted into an accommodation portion. The deformation guiding portion deforms the one end of the aerosol generating article when the aerosol generating article is inserted for the first time into the accommodation portion such that the aerosol generating device detects whether an aerosol generating article is being reused based on whether its end is deformed or not.

16 Claims, 15 Drawing Sheets

(56) References Cited

U.S. PATENT DOCUMENTS

| | | | |
|---|---|---|---|
| 9,814,265 | B2 | 11/2017 | Rinker et al. |
| 10,729,178 | B2 | 8/2020 | Reevell |
| 10,918,136 | B2 | 2/2021 | Reevell |
| 10,993,473 | B2 | 5/2021 | Malgat et al. |
| 11,330,835 | B2 | 5/2022 | Lavanchy |
| 2011/0192408 | A1 | 8/2011 | Inagaki et al. |
| 2015/0013696 | A1 | 1/2015 | Plojoux et al. |
| 2016/0302488 | A1 | 10/2016 | Fernando et al. |
| 2017/0071251 | A1 | 3/2017 | Goch |
| 2017/0143039 | A1 | 5/2017 | Buehler et al. |
| 2017/0191020 | A1 | 7/2017 | Recht et al. |
| 2017/0196268 | A1 | 7/2017 | Reevell |
| 2017/0231277 | A1 | 8/2017 | Mironov et al. |
| 2017/0340008 | A1 | 11/2017 | Sebastian et al. |
| 2018/0220713 | A1 | 8/2018 | Chang et al. |
| 2018/0228213 | A1 | 8/2018 | Buehler et al. |
| 2018/0235279 | A1 | 8/2018 | Wilke et al. |
| 2018/0242638 | A1 | 8/2018 | Godfrey et al. |
| 2019/0000141 | A1 | 1/2019 | Rojo-Calderon et al. |
| 2019/0014820 | A1 | 1/2019 | Malgat |
| 2019/0045844 | A1 | 2/2019 | Reevell |
| 2019/0230989 | A1 | 8/2019 | Fursa et al. |
| 2019/0261684 | A1 | 8/2019 | Reevell |
| 2020/0060340 | A1* | 2/2020 | Hejazi .................. A24B 15/167 |
| 2020/0093185 | A1 | 3/2020 | Lim |
| 2020/0154765 | A1 | 5/2020 | Lee et al. |
| 2020/0196665 | A1 | 6/2020 | Bilat et al. |
| 2020/0232766 | A1 | 7/2020 | Flick |
| 2020/0260790 | A1 | 8/2020 | Kaufman et al. |
| 2020/0305508 | A1 | 10/2020 | Talon |
| 2020/0316325 | A1 | 10/2020 | Reevell |
| 2021/0007400 | A1 | 1/2021 | Liu et al. |
| 2021/0076736 | A1 | 3/2021 | Fernando et al. |
| 2021/0237214 | A1 | 8/2021 | Guenther et al. |

FOREIGN PATENT DOCUMENTS

| | | | |
|---|---|---|---|
| CN | 106455726 A | 2/2017 | |
| CN | 106929402 A | 7/2017 | |
| CN | 107713009 A | 2/2018 | |
| CN | 107775187 A | 3/2018 | |
| CN | 107846978 A | 3/2018 | |
| CN | 107949287 A | 4/2018 | |
| CN | 108366618 A | 8/2018 | |
| CN | 108601396 A | 9/2018 | |
| CN | 109363243 A | 2/2019 | |
| CN | 109640717 A | 4/2019 | |
| CN | 209498553 U | 10/2019 | |
| DE | 20 2014 001 718 U1 | 7/2015 | |
| EP | 2 468 118 A1 | 6/2012 | |
| EP | 3 175 721 A1 | 6/2017 | |
| EP | 3 574 774 A1 | 12/2019 | |
| EP | 3 718 419 A1 | 10/2020 | |
| EP | 3 831 223 A1 | 6/2021 | |
| GB | 2 259 135 A | 3/1993 | |
| JP | 9-222361 A | 8/1997 | |
| JP | 11-6767 A | 1/1999 | |
| JP | 11-178561 A | 7/1999 | |
| JP | 2018-527918 A | 9/2018 | |
| JP | 2019-506855 A | 3/2019 | |
| KR | 10-0889660 B1 | 3/2009 | |
| KR | 10-2011-0096548 A | 8/2011 | |
| KR | 10-2013-0001750 A | 1/2013 | |
| KR | 10-2014-0067691 A | 6/2014 | |
| KR | 10-2014-0084769 A | 7/2014 | |
| KR | 10-2014-0121381 A | 10/2014 | |
| KR | 10-2015-0144089 A | 12/2015 | |
| KR | 10-2016-0096585 A | 8/2016 | |
| KR | 10-1776966 B1 | 9/2017 | |
| KR | 10-2018-0056643 A | 6/2018 | |
| KR | 10-2018-0099674 A | 9/2018 | |
| KR | 10-2018-0100319 A | 9/2018 | |
| KR | 10-2018-0120166 A | 11/2018 | |
| KR | 10-2018-0129637 A | 12/2018 | |
| KR | 10-2019-0011721 A | 2/2019 | |
| KR | 10-2019-0012150 A | 2/2019 | |
| KR | 10-1971169 B1 | 4/2019 | |
| KR | 10-2019-0051745 A | 5/2019 | |
| KR | 10-2019-0129757 A | 11/2019 | |
| KR | 10-2019-0134855 A | 12/2019 | |
| KR | 10-2019-0143177 A | 12/2019 | |
| KR | 10-2020-0000635 A | 1/2020 | |
| TW | 201618682 A | 6/2016 | |
| WO | 2016/026811 A1 | 2/2016 | |
| WO | WO-2017051006 A1 * | 3/2017 | ........... A24B 15/167 |
| WO | 2017/114895 A1 | 7/2017 | |
| WO | 2017/118557 A1 | 7/2017 | |
| WO | WO-2017147560 A1 * | 8/2017 | ............. A24F 40/50 |
| WO | 2018/050701 A1 | 3/2018 | |
| WO | 2018/190606 A1 | 10/2018 | |
| WO | 2019/090200 A1 | 5/2019 | |
| WO | 2019/129378 A1 | 7/2019 | |
| WO | 2019/197413 A1 | 10/2019 | |
| WO | 2019/224310 A1 | 11/2019 | |
| WO | WO-2020074595 A1 * | 4/2020 | ............. A24F 40/20 |

OTHER PUBLICATIONS

English machine translation of CN-108576927-A; Sep. 28, 2018; Liu; 18 pages. (Year: 2018).*

English machine translation of KR20190051745 (A); May 15, 2019; Seong; 12 pages. (Year: 2019).*

Tong Ying, "Research on the Key Technologies of Stereo Vision Based on Infrared and Visible Dual Band Images", China Doctoral Dissertation Full Text Database Information Technology Series, Tianjin University, 2015 (122 pages total).

Office Action issued Sep. 26, 2023 in Chinese Application No. 202080006491.4.

Written opinion for PCT/KR2020/017923 dated Mar. 16, 2021.

International search report for PCT/KR2020/017923 dated Mar. 16, 2021.

International Search Report dated Mar. 16, 2021 from the International Searching Authority in International Application No. PCT/KR2020/018035.

International Search Report dated Mar. 17, 2021 from the International Searching Authority in International Application No. PCT/KR2020/018171.

Office Action dated Jun. 21, 2022 issued by the Korean Patent Office in Korean Application No. 10-2020-0041538.

Office Action dated Jul. 19, 2022 issued by the Japanese Patent Office in Japanese Application No. 2021-534382.

Office Action dated Jul. 12, 2022 issued by the Japanese Patent Office in Japanese Application No. 2021-529309.

Office Action issued Dec. 15, 2021 in Korean Application No. 10-2020-0028582.

Office Action issued Dec. 15, 2021 in Korean Application No. 10-2020-0041537.

Office Action issued Dec. 17, 2021 in Korean Application No. 10-2020-0047420.

Extended European Search Report issued Nov. 5, 2021 in European Application No. 20855894.0.

Extended European Search Report issued Oct. 15, 2021 in European Application No. 20866967.1.

Extended European Search Report issued Dec. 8, 2021 in European Application No. 20866966.3.

Office Action dated Apr. 14, 2023 from the Chinese Patent Office in Application No. 202080006484.4.

Office Action dated Apr. 15, 2023 from the Chinese Patent Office in Application No. 202080006550.8.

Office Action dated Apr. 17, 2023 from the Chinese Patent Office in Application No. 202080006491.4.

European Office Action issued Mar. 13, 2024 in Application No. 20866967.1.

* cited by examiner (BEFORE INSERTION)

(AFTER INSERTION)

(BEFORE INSERTION)

(AFTER INSERTION)

AEROSOL GENERATING DEVICE

CROSS-REFERENCE TO RELATED APPLICATIONS

This application is a National Stage of International Application No. PCT/KR2020/017923 filed Dec. 9, 2020, which claims priority under U.S.C. § 119(a) to Korean Patent Application 10-2020-0001706 filed on Jan. 6, 2020 and Korean Patent Application No. 10-2020-0041537 filed on Apr. 6, 2020.

TECHNICAL FIELD

One or more embodiments relate to an aerosol generating device, and more particularly, to an aerosol generating device including a deformation guiding portion that comes into contact with one end of an aerosol generating article.

BACKGROUND ART

Recently, the need for alternatives to traditional cigarettes has increased. For example, there is growing demand for an aerosol generating device that generates aerosols by heating an aerosol generating material, rather than by combusting cigarettes. Accordingly, studies on a heating-type cigarette and a heating-type aerosol generating device have been actively conducted.

DISCLOSURE

Technical Problem

Users may insert an aerosol generating article into an aerosol generating device to smoke. Generally, an aerosol generating article manufactured for a single use is inserted into an aerosol generating device, used, and then discarded.

However, some users re-insert a used aerosol generating article without discarding it. The reuse of the aerosol generating article may cause discomfort to the user by changing the flavor of an aerosol generated from the aerosol generating article.

Thus, it is necessary to prevent the reuse of the aerosol generating article.

Technical Solution

One or more embodiments provide an aerosol generating device that deforms at least part of an aerosol generating article that is inserted in the aerosol generating device for the first time, such that reuse of the aerosol generating article is detected and prevented.

Technical solutions to be solved through embodiments are not limited to the above-described technical solutions, and other technical solutions may be inferred from the following embodiments.

Advantageous Effects

In an aerosol generating device according to one or more embodiments, when an aerosol generating article is first inserted, one end of the aerosol generating article is deformed by a deformation guiding portion that comes into contact with one end of the aerosol generating article. As one end of the aerosol generating article is deformed, the aerosol generating device may detect the reuse of the aerosol generating article.

When the reuse of the aerosol generating article is detected, the aerosol generating device may be blocked from operation. Alternatively, the reuse of the aerosol generating article may be notified to a user through an alarm unit installed in the aerosol generating device.

The satisfaction of the user may be prevented from being reduced due to changes in the flavor of an aerosol that may be caused by the reuse of the aerosol generating article.

BEST MODE

Figure 1:
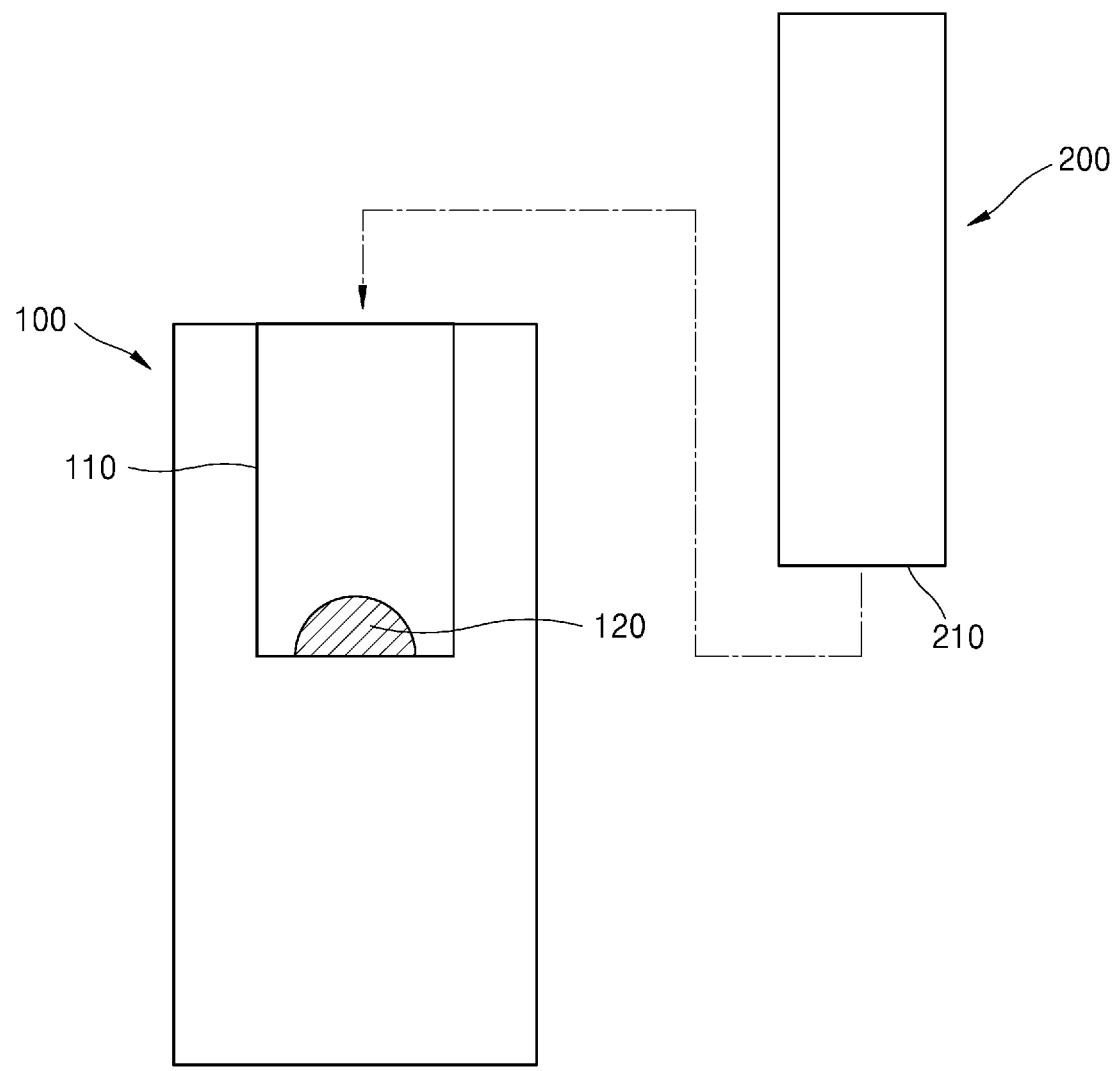
FIG. 1 is a cross-sectional view schematically showing an aerosol generating device and an aerosol generating article inserted into the aerosol generating device, according to an embodiment.

According to an embodiment, an aerosol generating device may include: an accommodation portion configured to accommodate an aerosol generating article through an opening; and a deformation guiding portion configured to come into contact with and deform one end of the aerosol generating article when the aerosol generating article is inserted into the accommodation portion.

The deformation guiding portion may have a shape of part of a sphere protruding toward the opening, a pyramid, a cone, a truncated pyramid, a truncated cone, or a rod having a pointed tip.

A maximum diameter of the deformation guiding portion may be greater than a minimum diameter of a hole formed in the one end of the aerosol generating article, and the deformation guiding portion may be configured to deform the one end of the aerosol generating article by being inserted into the hole when the aerosol generating article is inserted into the accommodation portion.

The aerosol generating device may further include a sensor configured to detect deformation of the one end of the aerosol generating article.

The sensor may be adjacent to the deformation guiding portion.

The sensor may include: an emission portion configured to emit light or ultrasonic waves toward the one end of the aerosol generating article; and a detection portion configured to receive light or ultrasonic waves reflected from the one end of the aerosol generating article after being emitted from the emission portion.

The sensor may be configured to generate a deformation detection signal based on the deformation of the one end of the aerosol generating article being detected.

The deformation guiding portion may be pressed with a first pressure when an aerosol generating article having no deformed end is inserted, the deformation guiding portion may be pressed by a second pressure when an aerosol generating article having a deformed end is inserted, and the first pressure is greater than the second pressure.

The deformation guiding portion may be configured to generate a deformation detection signal based on being pressed with the second pressure.

The deformation guiding portion may include a pressure sensor configured to measure pressure applied on the deformation guiding portion, and the deformation guiding portion may be configured to generate a deformation detection signal based on the pressure sensor detecting that the deformation guiding portion is pressed with the second pressure.

The aerosol generating device may further include a controller configured to control the aerosol generating device based on the deformation detection signal.

The controller may be configured to block the operation of the aerosol generating device based on receiving the deformation detection signal.

The controller may be configured to generate an alarm signal notifying a user of reuse of the aerosol generating article based on receiving the deformation detection signal.

The aerosol generating device may further include an alarm unit comprising at least one of a vibration unit, a speaker unit, and a display unit, and configured to output at least one of vibration, sound, and an optical signal according to the alarm signal.

MODE FOR INVENTION

With respect to the terms in the various embodiments, the general terms which are currently and widely used are selected in consideration of functions of structural elements in the various embodiments of the present disclosure. However, meanings of the terms can be changed according to intention, a judicial precedence, the appearance of a new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

The terms "embodiment" or "embodiments" described in the specification are intended to explain the inventive concept clearly. Therefore, embodiments should not be construed to be exclusive to each other. For example, elements explained in relating to an embodiment may be embodied and applied in many different forms within the scope of the specification.

In addition, terms used in the present specification are for describing the embodiments and are not intended to limit the embodiments. In the present specification, the singular form also includes the plurality form unless specifically stated in the phrase.

Throughout the specification, the "longitudinal direction" of a component may be a direction in which the component extends along an axis in one direction of the component, wherein the axis in one direction of the component extends longer than an axis in the other direction of the component crossing the axis in one direction of the component.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element or layer is referred to as being "over," "above," "on," "connected to" or "coupled to" another element or layer, it can be directly over, above, on, connected or coupled to the other element or layer or intervening elements or layers may be present. In contrast, when an element is referred to as being "directly over," "directly above," "directly on," "directly connected to" or "directly coupled to" another element or layer, there are no intervening elements or layers present. Like numerals refer to like elements throughout.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

FIG. 1 is a cross-sectional view schematically showing an aerosol generating device 100 and an aerosol generating article 200 inserted into the aerosol generating device 100, according to an embodiment.

The aerosol generating device 100 may include an accommodation portion 110 for accommodating the aerosol generating article 200 through an opening and a deformation guiding portion 120 that comes into contact with one end 210 of the aerosol generating article 200 when the aerosol generating article 200 is inserted into the accommodation portion 110.

The deformation guiding portion 120 of the aerosol generating device 100 may deform one end 210 of the aerosol generating article 200 when the aerosol generating article 200 is inserted into the accommodation portion 110 for the first time.

The aerosol generating article 200 and the accommodation portion 110 may have shapes corresponding to each other. For example, when the aerosol generating article 200 has a cylindrical shape, the accommodation portion 110 may have a cylindrical shape so as to accommodate the aerosol generating article 200. However, the shapes of the aerosol generating article 200 and the accommodation portion 110 are not limited thereto and may be changed as needed.

The aerosol generating device 100 may include the deformation guiding portion 120. The deformation guiding portion 120 may be formed on a bottom surface of the accommodation portion 110, for example. The deformation guiding portion 120 may be a portion extending from the bottom surface of the accommodation portion 110 in a longitudinal direction of the accommodation portion 110. For example, the deformation guiding portion 120 may be a protrusion protruding from the bottom surface of the accommodation portion 110 by a certain distance.

The deformation guiding portion 120 may include materials having elasticity. When the deformation guiding portion 120 is pressed, a certain portion of the deformation guiding portion 120 may be compressed. The deformation guiding portion 120 may have a rigidity of a certain range or more so as to deform one end 210 of the aerosol generating article 200.

The deformation guiding portion 120 may come into contact with one end 210 of the aerosol generating article 200 when the aerosol generating article 200 is inserted. When the deformation guiding portion 120 is formed on the bottom surface of the accommodation portion 110, one end 210 of the aerosol generating article 200 may be a portion facing the bottom surface of the accommodation portion 110 of the aerosol generating article 200.

When the aerosol generating article 200 is inserted into the accommodation portion 110 for the first time, the deformation guiding portion 120 may come into contact with one end 210 of the aerosol generating article 200 so as to deform one end of the aerosol generating article 200. That is, as the deformation guiding portion 120 has a rigidity of a certain range or more so to deform one end 210 of the aerosol generating article 200, one end 210 of the aerosol generating article 200 may receive an external force from the deformation guiding portion 120 when coming contact with the deformation guiding portion 120. According to the external force from the deformation guiding portion 120, one end 210 of the aerosol generating article 200 may be deformed.

For example, when the aerosol generating article 200 has a cylindrical shape and one end 210 of the aerosol generating article 200 is a bottom portion of a cylinder, the bottom surface of the cylinder that is one end 210 of the aerosol generating article 200 may come into contact with the deformation guiding portion 120. The deformation guiding portion 120 may be inserted into the aerosol generating article 200 through the bottom surface of the cylinder that is one end 210 of the aerosol generating article 200. Insertion of the deformation guiding portion 120 may compress one end 210 of the aerosol generating article 200. Thus, one end 210 may be deformed.

The cross-sectional area of one end 210 of the aerosol generating article 200 may be greater than that of the deformation guiding portion 120. Thus, the deformation guiding portion 120 may be completely inserted into one end 210 of the aerosol generating article 200.

FIGS. 2A through 2E are cross-sectional views showing exemplary aspects of the deformation guiding portion 120 of the aerosol generating device 100 according to an embodiment.

Figure 2A:
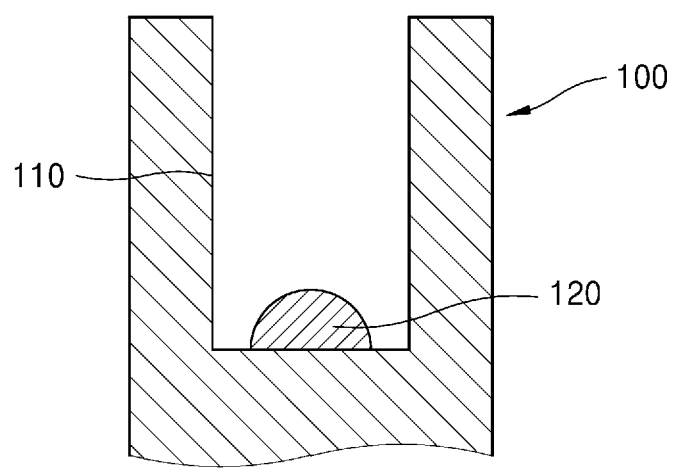
FIGS. 2A through 2E are cross-sectional views of a deformation guiding portion of an aerosol generating device according to embodiments.

Example shapes of the deformation guiding portion 120 are shown in FIGS. 2A through 2E. The deformation guiding portion 120 may be, for example, a hemispheric shape that is part of a sphere, as shown in FIG. 2A.

Figure 2B:
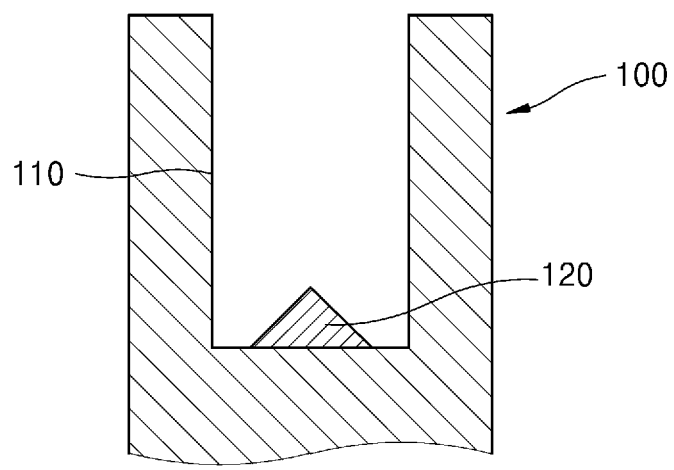

As shown in FIG. 2B, the deformation guiding portion 120 may be, for example, a pyramid or a cone extending in the longitudinal direction of the accommodation portion 110.

Figure 2C:
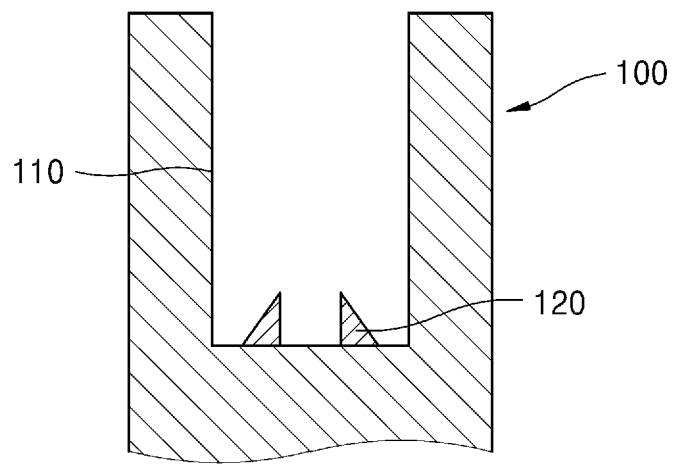

The deformation guiding portion 120 may have a shape of a pyramid or a cone including a hollow, as shown in FIG. 2C, for example. In this case, the hollow may have a cylindrical shape, and the configuration or the aerosol generating device 100 or an electric wire for electrical connection may pass through the hollow and extend to the accommodation portion 110.

Figure 2D:
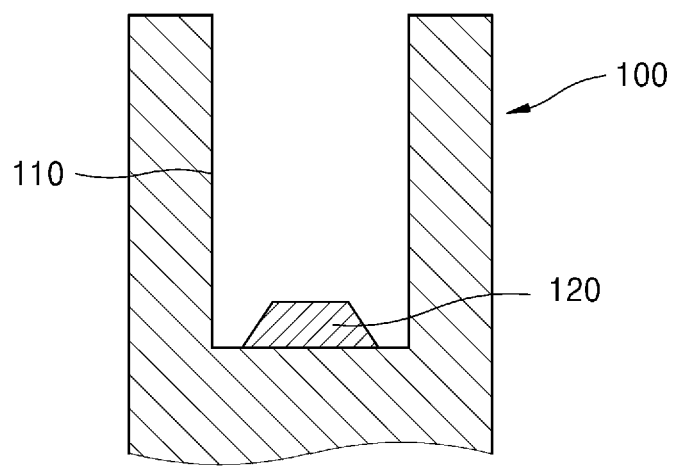

The deformation guiding portion 120 may have a truncated pyramid shape or a truncated cone, as shown in FIG. 2D. The truncated cone or pyramid may extend in the longitudinal direction of the accommodation portion 110. In other words, the deformation guiding portion 120 that comes into contact with the aerosol generating article 200 may have a frustum shape.

Figure 2E:
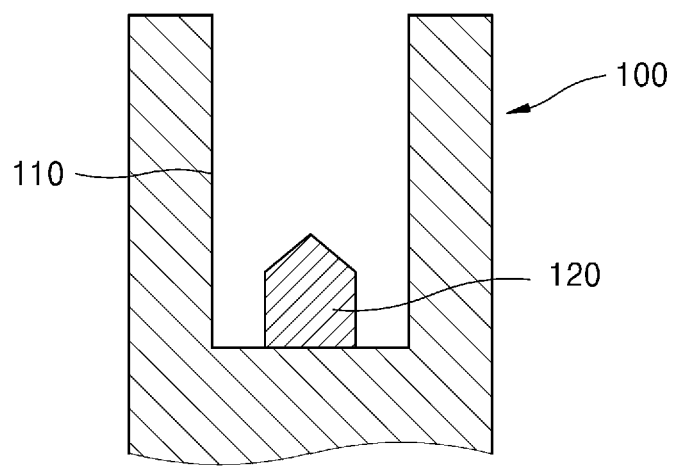

The deformation guiding portion 120 may have, for example, a shape of a rod having a pointed tip as shown in FIG. 2E. For example, the deformation guiding portion 120 may have a shape formed by combining a cylinder or prism with a cone or pyramid. For example, a cylinder may extend from the bottom surface of the accommodation portion 110, and a cone may be combined with the cylinder at the top of the cylinder.

FIGS. 3A, 3B, 3C and 3D are views schematically showing how one end of an aerosol generating article is deformed after the aerosol generating article is inserted into an aerosol generating device for the first time, according to embodiments.

Figure 3A:
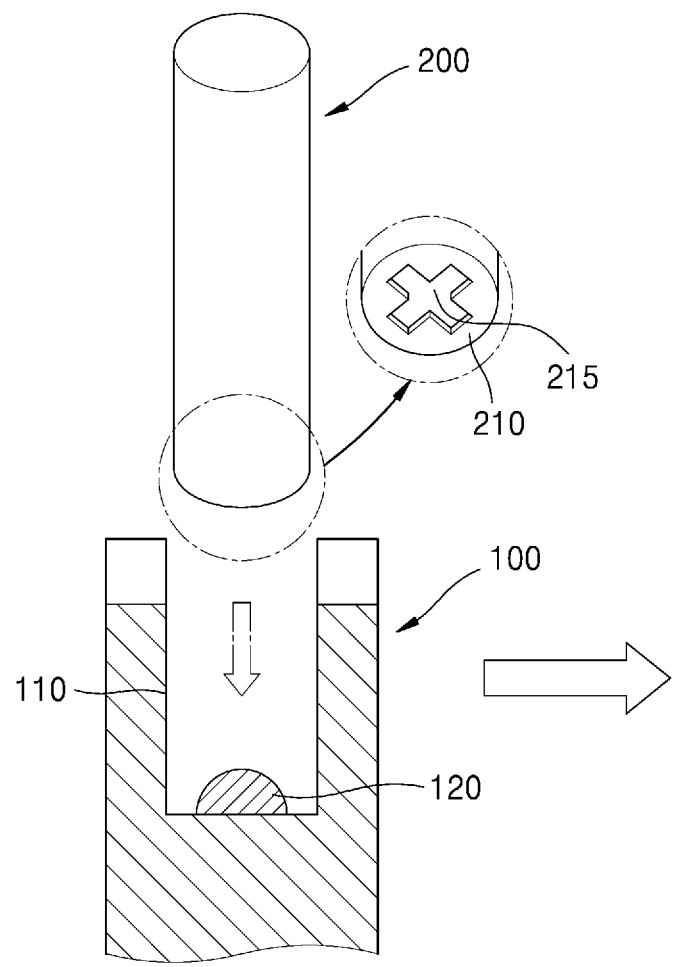
FIGS. 3A, 3B, 3C and 3D are views schematically showing how one end of an aerosol generating article is deformed after the aerosol generating article is first inserted into an aerosol generating device, according to embodiments.
Figure 3B:
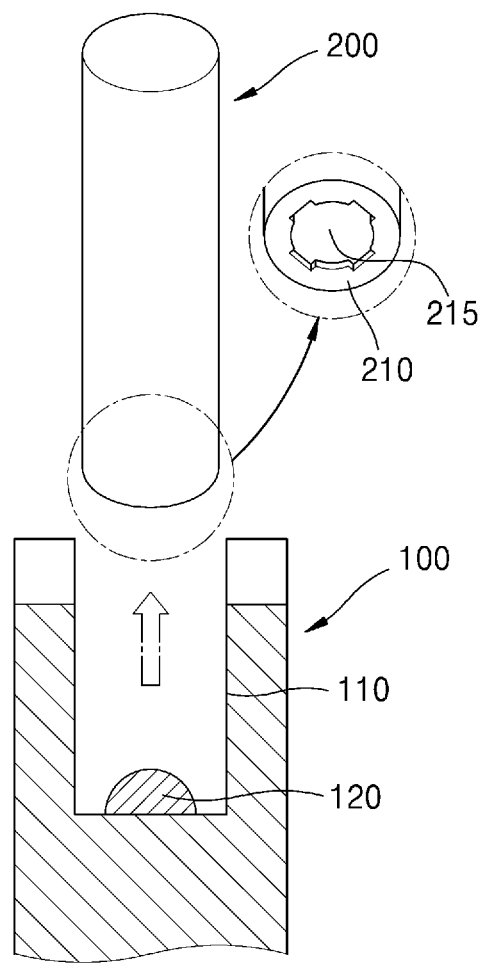

In the example shown in FIGS. 3A and 3B, the aerosol generating article 200 having a hole 215 formed in one end 210 of the aerosol generating article 200 is inserted into the aerosol generating device 100 for the first time.

As shown in FIGS. 3A and 3B, the hole 215 may be formed in one end 210 of the aerosol generating article 200. The hole 215 may be formed inside the aerosol generating article 200. The hole 215 may be a space extending from one end 210 of the aerosol generating article 200 toward the other end of the aerosol generating article 200 by a certain distance. The shape and size of the hole 215 may be changed as needed. The hole 215 may have different shapes and sizes according to the type of the aerosol generating article 200.

When the aerosol generating article 200 having the hole 215 formed in one end 210 is inserted into the aerosol generating device 100 for the first time, as the size of the hole 215 is changed, one end 210 of the aerosol generating article 200 may be deformed. For example, when the aerosol generating article 200 is inserted into the accommodation portion 110, the deformation guiding portion 120 may be inserted into the through hole 215. A maximum diameter of the deformation guiding portion 120 may be greater than a minimum diameter of the through hole 215. The size of the hole 215 may increase according to a difference in diameters of the deformation guiding portion 120 and the hole 215. One end 210 of the aerosol generating article 200 may be deformed according to the size of the through hole 215.

Figure 3C:
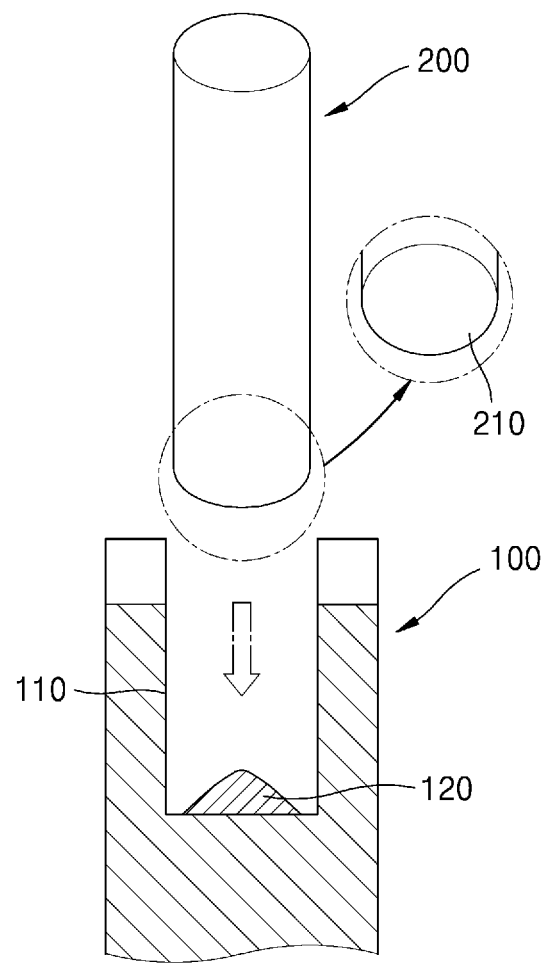
Figure 3D:
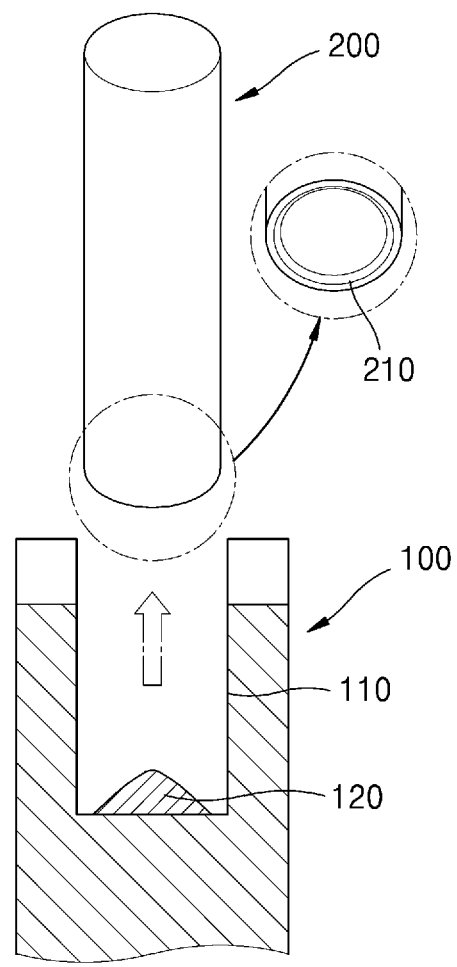

FIGS. 3C and 3D schematically shows how one end of an aerosol generating article is deformed after the aerosol generating article is inserted into an aerosol generating device for the first time, according to another embodiment.

In the example shown in FIGS. 3C and 3D, the aerosol generating article 200 having no through hole in one end 210 is inserted into the aerosol generating device 100 for the first time.

As shown in FIGS. 3C and 3D, one end of the aerosol generating article 200 may have a closed shape. When the aerosol generating article 200 is first inserted into the aerosol generating device 100, the deformation guiding portion 120 may be inserted into the aerosol generating article 200 through one end 210 of the aerosol generating article 200. Accordingly, a depression may be formed in one end 210 of the aerosol generating article 200. The depression may be formed to correspond to the shape of the deformation guiding portion 120. According to the formation of the depression, one end 210 of the aerosol generating article 200 may be deformed.

Figure 4:
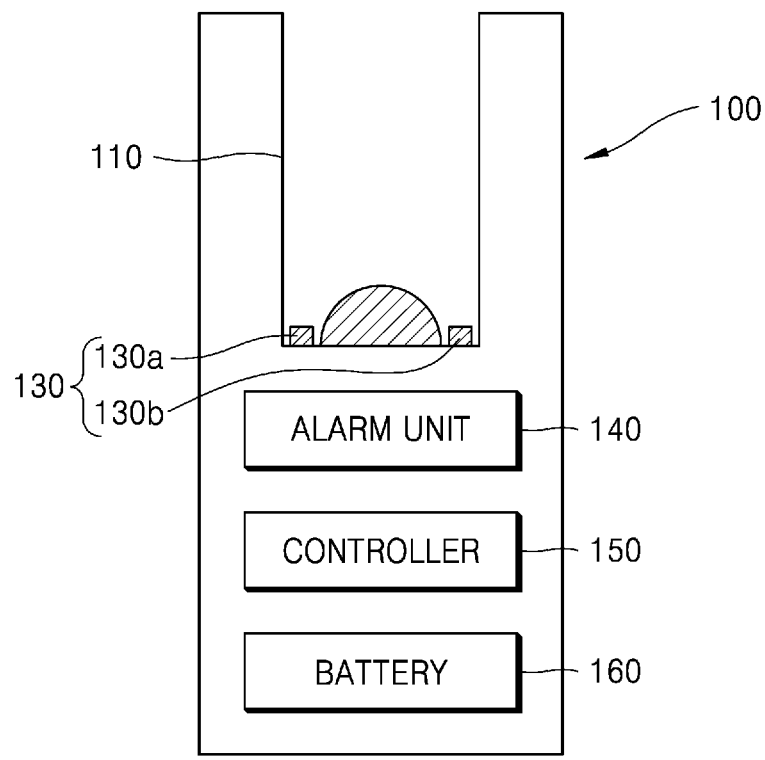
FIG. 4 is a cross-sectional view of an aerosol generating device according to an embodiment.

FIG. 4 is a cross-sectional view of an aerosol generating device 100 according to an embodiment.

The aerosol generating device 100 according to the present embodiment may further include a sensor 130 that detects deformation of one end 210 of the aerosol generating article 200.

Detection of the initial insertion and reinsertion of the aerosol generating article 200 may be performed in various ways. The aerosol generating device 100 may determine whether the aerosol generating article 200 is inserted, through the deformation guiding portion 120 that comes into contact with the aerosol generating article 200 or an inductance sensor (not shown) mounted on the accommodation portion 110.

Referring to FIGS. 3A-3B, when the aerosol generating article 200 is inserted into the accommodation portion 110 for the first time, one end 210 of the aerosol generating article 200 may come into contact with the deformation guiding portion 120 and may be deformed. After one end 210 of the aerosol generating article 200 is deformed according to the initial insertion, when the aerosol generating article 200 is re-inserted into the accommodation portion 110, the sensor 130 may detect deformation of one end 210 of the aerosol generating article 200.

As an example, the sensor 130 may measure the height of one end 210 of the aerosol generating article 200, thereby detecting deformation of one end 210. When the aerosol generating article 200 is inserted for the first time, a depression may be formed to correspond to the shape of the deformation guiding portion 120.

The height of the depression may vary according to a distance from the center of the aerosol generating article 200. For example, the height of the depression may be the greatest at the center of the aerosol generating article 200 and may decrease as the distance from the center of the aerosol generating article 200 increases. When the aerosol generating article 200 is re-inserted into the accommodation portion 110, the sensor 130 may measure a difference in heights of portions of the depression, thereby detecting deformation of one end 210.

As another example, the sensor 130 may measure the shape of one end 210 of the aerosol generating article 200, thereby detecting deformation of one end 210. The shape of the aerosol generating article 200 may be a preset shape, for example, a cylindrical shape, and one end 210 of the aerosol generating article 200 may correspond to a bottom of a cylinder.

After the aerosol generating article 200 is inserted for the first time, one end 210 of the aerosol generating article 200 may be deformed to have a shape corresponding to the shape of the deformation guiding portion 120. When the aerosol generating article 200 is re-inserted into the accommodation portion 110, the sensor 130 may compare the preset shape of one end 210 of the aerosol generating article 200 with the shape of the aerosol generating article 200 inserted into the accommodation portion 110, thereby detecting deformation of one end 210.

The sensor 130 may be adjacent to the deformation guiding portion 120. For example, the sensor 130 may be disposed on the bottom surface of the accommodation portion 110 together with the deformation guiding portion 120, and a plurality of sensors 130 may be arranged around the deformation guiding portion 120.

The sensor 130 may include an emission portion 130a that emits light or ultrasonic waves toward one end 210 of the aerosol generating article 200 and a detection portion 130b that receives light or ultrasonic waves reflected from one end 210 of the aerosol generating article 200 after being emitted from the emission portion 130a.

When the aerosol generating article 200 is inserted, the emission portion 130a of the sensor 130 may emit light or ultrasonic waves toward one end 210 of the aerosol generating article 200. Alternatively, the emission portion 130a may periodically emit light or ultrasonic waves toward one end 210 of the aerosol generating article 200. At this time, a period in which light or ultrasonic waves are emitted, may be preset.

Light or ultrasonic waves emitted from the emission portion 130a may be reflected from one end 210 of the aerosol generating article 200. The reflected light or ultrasonic waves may return to the sensor 130, and the detection portion 130b of the sensor 130 may receive the reflected light or ultrasonic waves.

The detection portion 130b that receives the reflected light or ultrasonic waves may detect deformation of one end 210 of the aerosol generating article 200. The sensor 130 may generate a deformation detection signal when deformation of one end 210 is detected.

The aerosol generating device 100 may further include a battery 160 and a controller 150.

The battery 160 may supply power used to operate the aerosol generating device 100. For example, the battery 160 may supply power to heat a heater (not shown) for transferring heat to the aerosol generating article 200. Also, the battery 160 may supply power required to operate a sensor, a motor, or the like that may be installed in the aerosol generating device 100.

The controller 150 may control the overall operation of the aerosol generating device 100. In detail, the controller 150 may control the battery 160, thereby operating the aerosol generating device 100. The controller 150 may control the operation of other configurations included in the aerosol generating device 100. Also, the controller 150 may check the state of each of the configurations of the aerosol generating device 100, thereby determining whether the aerosol generating device 100 is in an operable state.

The controller 150 may include at least one processor. A processor can be implemented as an array of a plurality of logic gates or can be implemented as a combination of a general-purpose microprocessor and a memory in which a program executable in the microprocessor is stored. In addition, it can be understood by those of ordinary skill in the art that this embodiment may be implemented with other types of hardware.

The controller 150 may be electrically connected to the sensor 130 and may control the overall operation of the aerosol generating device 100. When the sensor 130 detects deformation of one end 210 of the aerosol generating article 200, the sensor 130 may transmit a deformation detection signal to the controller 150.

The deformation detection signal may be generated when the aerosol generating article 200 is re-inserted into the accommodation portion 110. Once the aerosol generating article 200 is used, one end 210 of the aerosol generating article 200 may be deformed. When the aerosol generating article 200 including the deformed one end 210 is inserted into the accommodation portion 110, such deformation of one end 210 may be detected by the sensor 130.

On detecting deformation of one end 210, the sensor 130 may generate a deformation detection signal and transmit the deformation detection signal to the controller 150. When the controller 150 receives the deformation detection signal from the sensor 130, the controller 150 may detect the reuse of the aerosol generating article 200 and block operation of the aerosol generating device 100.

As another example, when the sensor 130 does not detect deformation of one end of the aerosol generating article 200, the sensor 130 may transmit a deformation non-detection signal to the controller 150. When the deformation non-detection signal is transmitted from the sensor 130, the controller 150 may recognize the initial use of the aerosol generating article 200 and allow the aerosol generating device 100 to be normally operated.

Transmission of the deformation detection signal to the controller 150 may be one of conditions under which the aerosol generating device 100 may be normally operated. That is, the normal operation of the aerosol generating device 100 may be determined depending on whether the deformation detection signal is transmitted from the sensor 130 to the controller 150.

As an example, when the deformation detection signal is transmitted from the sensor 130 to the controller 150, the controller 150 may control power output of the battery 160 to block the normal operation of the aerosol generating device 100.

As another example, when the deformation detection signal is transmitted from the sensor 130 to the controller 150, the controller 150 may generate an alarm signal notifying the user of the reuse of the aerosol generating article 200.

To this end, the aerosol generating device 100 may further include an alarm unit 140. The alarm unit 140 may include at least one of a vibration unit, a speaker unit, and a display unit, and the alarm unit 140 may be mounted on the aerosol generating device 100 to notify the user of the state of the aerosol generating device 100. The alarm unit 140 may transmit at least one of vibration, sound, and an optical signal according to the alarm signal of the controller 150.

For example, the display unit 140 may be mounted as the alarm unit 140 in the aerosol generating device 100. In this case, as the aerosol generating article 200 including the deformed one end 210 is inserted, the deformation detection signal may be transmitted to the controller 150 is transmitted, and the controller 150 may generate an alarm signal notifying the user of the reuse of the aerosol generating article 200.

The alarm signal generated by the controller 150 may be transmitted to the display unit that is the alarm unit 140, and the display unit may display a visible information notifying the user of the reuse of the aerosol generating article 200. In this case, the visible information may include a certain image or text through which the user may recognize the reuse of the aerosol generating article 200.

Figure 5A:
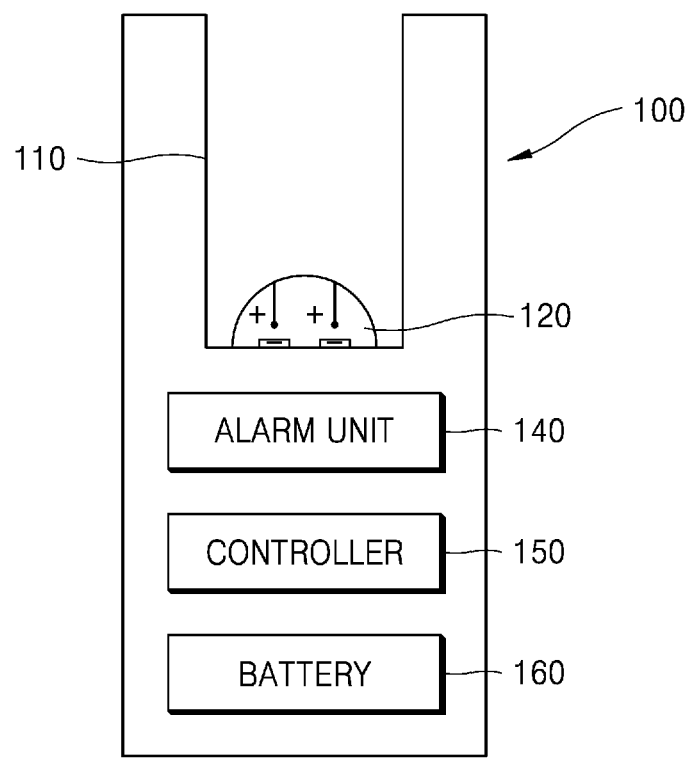
FIGS. 5A and 5B are cross-sectional views of an aerosol generating device according to another embodiment.
Figure 5B:
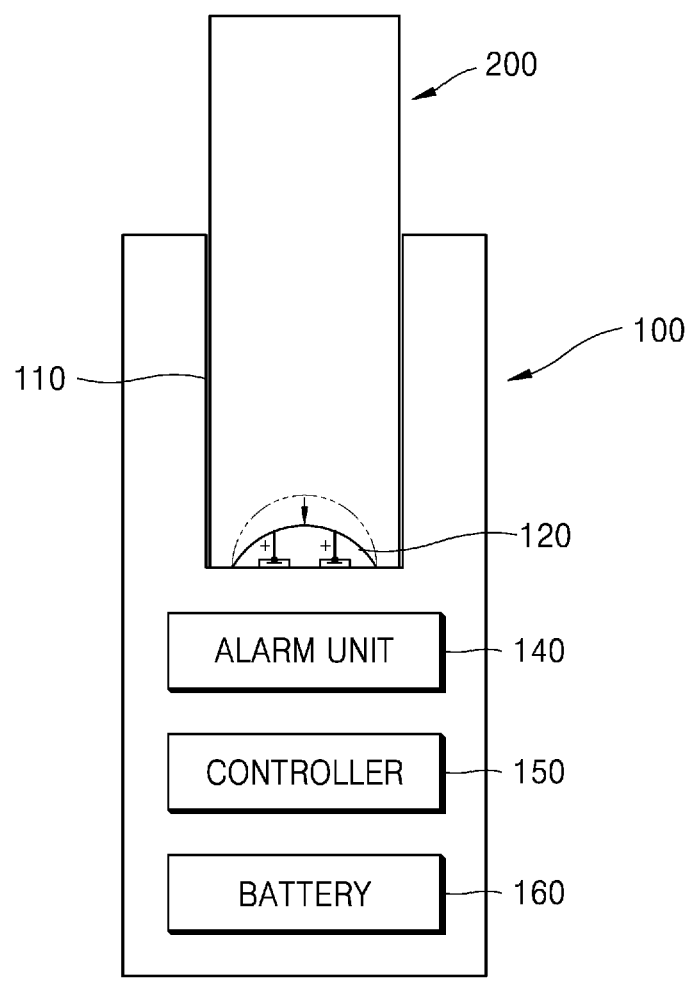

FIGS. 5A and 5B are cross-sectional views of an aerosol generating device 100 according to another embodiment.

A deformation guiding portion 120 of the aerosol generating device 100 according to the present embodiment may distinguish between the initial insertion and re-insertion of the aerosol generating article 200 according to pressure applied on the deformation guiding portion 120.

When the aerosol generating article 200 is inserted for the first time into the accommodation portion 110, one end 210 of the aerosol generating article 200 may come into contact with the deformation guiding portion 120 and may be deformed. Deformation of one end 210 of the aerosol generating article 200 may correspond to the shape of the deformation guiding portion 120. Thus, deformation of one end 210 according to the initial insertion of the aerosol generating article 200 may change the pressure applied one end 210 of the aerosol generating article 200 on the deformation guiding portion 120.

That is, when the aerosol generating article 200 is inserted for the first time, the deformation guiding portion 120 may be pressed by one end 210 with a first pressure, and when the aerosol generating article 200 is re-inserted, the deformation guiding portion 120 may be pressed by one end 210 with a second pressure. In this case, the first pressure may be greater than the second pressure.

The first pressure and the second pressure may differ according to the type of the aerosol generating article 200. In this case, the range of pressures may be predetermined stored as data in the controller 150 of the aerosol generating device 100.

As shown in FIG. 5B, the deformation guiding portion 120 may be implemented as a membrane switch type and compressed according to external pressure.

In this case, when the deformation guiding portion 120 is pressed with a first pressure, the deformation guiding portion 120 may be compressed equal to or greater than a certain degree. When the deformation guiding portion 120 is compressed equal to or greater than a certain degree, the deformation guiding portion 120 may generate a deformation non-detection signal.

When the deformation guiding portion 120 is pressed with a second pressure that is smaller than the first pressure, the deformation guiding portion 120 may be compressed within a certain range and may generate a deformation detection signal.

For example, when the deformation guiding portion 120 is pressed with the first pressure, the height of the deformation guiding portion 129 may be decreased by a first distance greater than or equal to a threshold, and when the deformation guiding portion 120 is pressed with the second pressure, the height of the deformation guiding portion 120 may be decreased by a second distance less than the threshold. The threshold may be determined by repeated experiments and may differ according to the type of the aerosol generating article 200.

When the deformation guiding portion 120 is compressed such that its height is decreased by the threshold or more, the deformation guiding portion 120 may generate a deformation non-detection signal. On the other hand, when the deformation guiding portion 120 is compressed such that its height is decreased by less than the threshold, the deformation guiding portion 120 may generate a deformation detection signal. For example, if the deformation guiding portion 120 is not decreased at all (i.e., the second distance is zero), the deformation guiding portion 120 may generate a deformation detection signal.

The deformation detection signal generated from the deformation guiding portion 120 may be transmitted to the controller 150. When the controller 150 receives the deformation detection signal from the deformation guiding portion 120, the controller 150 may detect the reuse of the aerosol generating article 200 and block operation of the aerosol generating device 100.

Generation of the deformation non-detection signal or absence of the deformation detection signal may be one of conditions under which the aerosol generating device 100 may operate normally. That is, the normal operation of the aerosol generating device 100 may be determined according to whether a deformation detection signal is transmitted from the deformation guiding portion 120 to the controller 150.

As an example, when the deformation detection signal is transmitted from the deformation guiding portion 120 to the controller 150, the controller 150 may control power output of the battery 160 to block the normal operation of the aerosol generating device 100.

As another example, when the deformation detection signal is transmitted from the deformation guiding portion 120 to the controller 150, the controller 150 may generate an alarm signal notifying the user of the reuse of the aerosol generating article 200.

The alarm signal generation of the controller 150 according to the deformation detection signal and output of the alarm unit 140 according to the alarm signal are described above and thus, a detailed description will be omitted herein.

Figure 6A:
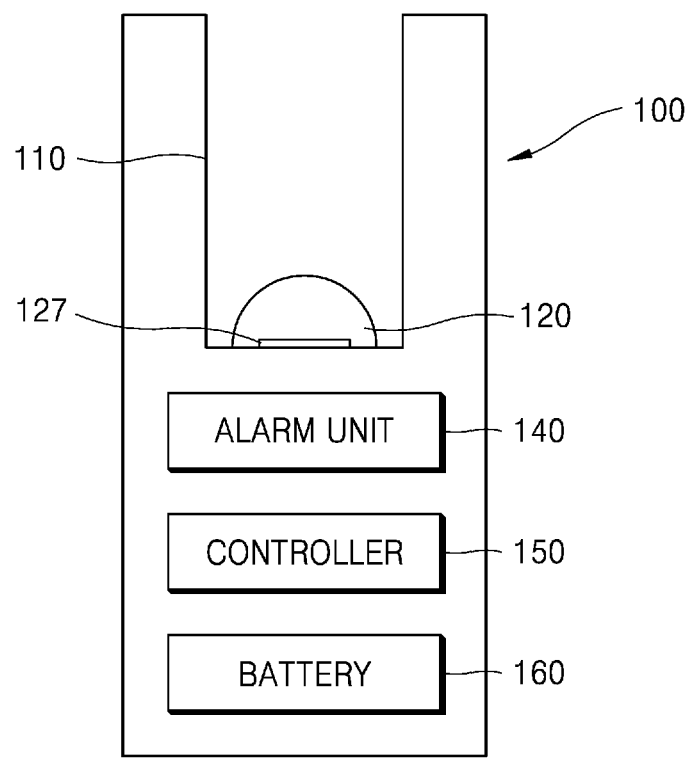
FIGS. 6A and 6B are cross-sectional views of an aerosol generating device according to another embodiment.
Figure 6B:
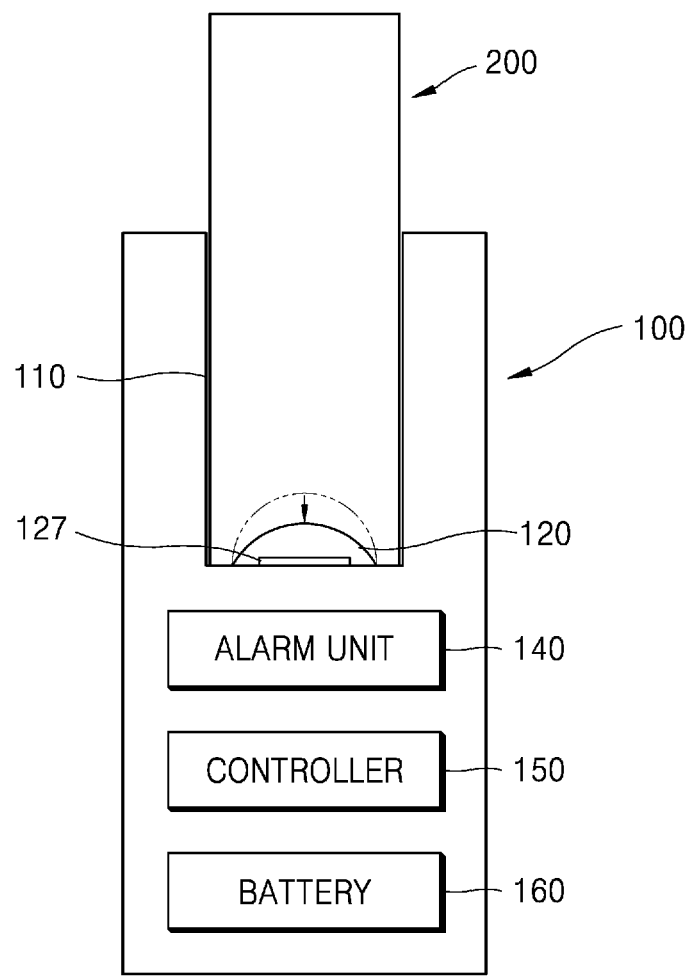

FIGS. 6A and 6B are cross-sectional views of an aerosol generating device 100 according to another embodiment.

The aerosol generating device 100 according to the present embodiment may include a pressure sensor 127 for measuring pressure. When the pressure applied on the deformation guiding portion 120 by one end 210 is measured by the pressure sensor 127 as being smaller than a threshold pressure, the deformation guiding portion 120 may generate a deformation detection signal.

In the aerosol generating device 100 according to an embodiment, the pressure sensor 127 may be included in the deformation guiding portion 120. In this case, the pressure sensor 127 may measure pressure applied on the deformation guiding portion 120 by the deformation guiding portion 120, and determine whether the measured pressure is smaller than the threshold pressure.

If the measured pressure is greater than or equal to the threshold pressure, the deformation guiding portion 120 may generate a deformation non-detection signal. On the other hand, if the measured pressure is smaller than the threshold pressure, the deformation guiding portion 120 may generate a deformation detection signal.

The deformation detection signal generated by the deformation guiding portion 120 may be transmitted to the controller 150. When the controller 150 receives the deformation detection signal from the deformation guiding portion 120, the controller 150 may detect the reuse of the aerosol generating article 200 and block operation of the aerosol generating device 100 or may generate an alarm signal notifying the user of the reuse of the aerosol generating article 200.

The operation of generating the alarm signal and outputting the alarm unit 140 is described above and thus, a detailed description will be omitted herein.

The aerosol generating device 100 according to one or more embodiments may deform one end 210 of the aerosol generating article 200 through the deformation guiding portion 120 that comes into contact with one end 210 of the aerosol generating article 200 when the aerosol generating article 200 is inserted for the first time. As one end 210 of the aerosol generating article 200 is deformed, the aerosol generating device 100 may detect the reuse of the aerosol generating article 200.

When the reuse of the aerosol generating article 200 is detected, the operation of the aerosol generating device 100 may be blocked. Alternatively, the reuse of the aerosol generating article 200 may be notified to the user through the alarm unit 40 installed in the aerosol generating device 100.

Accordingly, the aerosol generating device 100 may prevent the user from unintentionally reusing a single-use aerosol generating article, which causes altered flavor of the aerosol.

At least one of the components, elements, modules or units (collectively "components" in this paragraph) represented by a block in the drawings, such as the controller 150 and the alarm unit 140, may be embodied as various numbers of hardware, software and/or firmware structures that execute respective functions described above, according to an exemplary embodiment. For example, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Further, although a bus is not illustrated in the above block diagrams, communication between the components may be performed through the bus. Functional aspects of the above exemplary embodiments may be implemented in algorithms that execute on one or more processors. Furthermore, the components represented by a block or processing steps may employ any number of related art techniques for electronics configuration, signal processing and/or control, data processing and the like.

Those of ordinary skill in the technical field related to the present embodiments will appreciate that it may be implemented in a modified form without departing from the essential characteristics of the above-described description. The disclosed methods should be considered in a descriptive sense only and not for purposes of limitation. The scope of the present disclosure is shown in the claims rather than the forging description, and all differences within the scope equivalent thereto should be construed as being included in the present disclosure.

INDUSTRIAL APPLICABILITY

One or more embodiments relate to an aerosol generating device including a deformation guiding portion that comes into contact with one end of the aerosol generating article.

The invention claimed is:

1. An aerosol generating device comprising:
a first body configured to accommodate an aerosol generating article through an opening of the first body;
at least one second body configured to contact with and physically deform one end of the aerosol generating article, as a direct result of a mechanical interaction of contacting the one end, when the aerosol generating article is inserted into the first body; and
a sensor configured to detect, by detecting physical deformation of the one end of the aerosol generating article when the aerosol generating article is re-inserted into the first body, whether the one end of the aerosol generating article has been previously physically deformed by the mechanical interaction by the at least one second body during a prior insertion of the aerosol generating article into the first body.

2. The aerosol generating device of claim 1, wherein the at least one second body has a shape of a protrusion toward the opening.

3. The aerosol generating device of claim 1, wherein the at least one second body has a shape of part of a sphere, a pyramid, a cone, a truncated pyramid, a truncated cone, or a rod having a pointed tip.

4. The aerosol generating device of claim 1, wherein
a maximum diameter of the at least one second body is greater than a minimum diameter of a hole formed in the one end of the aerosol generating article, and
the at least one second body is configured to deform the one end of the aerosol generating article by being inserted into the hole when the aerosol generating article is inserted into the first body.

5. The aerosol generating device of claim 1, wherein the sensor is adjacent to the at least one second body.

6. The aerosol generating device of claim 1, wherein the sensor comprises:
an emission portion configured to emit light or ultrasonic waves toward the one end of the aerosol generating article; and
a detection portion configured to receive light or ultrasonic waves reflected from the one end of the aerosol generating article after being emitted from the emission portion.

7. The aerosol generating device of claim 1, wherein the sensor is configured to generate a deformation detection signal based on the deformation of the one end of the aerosol generating article being detected.

8. The aerosol generating device of claim 1, wherein,
the at least one second body is configured to be pressed and decreased by a first distance when the aerosol generating article having no deformed end is inserted,
the at least one second body is configured to be pressed and decreased by a second distance when the aerosol generating article having a deformed end is inserted, and
the first distance is greater than the second distance.

9. The aerosol generating device of claim 8, wherein the at least one second body is configured to generate a deformation detection signal based on being decreased by the second distance.

10. The aerosol generating device of claim 8, wherein
the sensor is a pressure sensor that is within the at least one second body,
the pressure sensor is configured to measure pressure applied on the at least one second body, and
the at least one second body is configured to generate a deformation detection signal based on the pressure sensor detecting that the at least one second body is decreased by the second distance.

11. The aerosol generating device of claim 7, further comprising a controller configured to control the aerosol generating device based on the deformation detection signal.

12. The aerosol generating device of claim 11, wherein the controller is configured to block operation of the aerosol generating device based on receiving the deformation detection signal.

13. The aerosol generating device of claim 11, wherein the controller is configured to generate an alarm signal notifying a user of reuse of the aerosol generating article based on receiving the deformation detection signal.

14. The aerosol generating device of claim 13, further comprising an alarm unit comprising at least one of a vibration unit, a speaker unit, and a display unit, and configured to output at least one of vibration, sound, and an optical signal according to the alarm signal.

15. The aerosol generating device of claim 1, wherein the sensor is configured to detect the deformation of the one end of the aerosol generating article by measuring:
a height of a depression in the one end of the aerosol generating article; or
a shape of the one end of the aerosol generating article; or
a pressure applied onto the sensor due to re-insertion of the aerosol generating article is into the first body.

16. An aerosol generating device comprising:
a first body configured to accommodate an aerosol generating article through an opening of the first body;
at least one second body configured to contact with and deform one end of the aerosol generating article when the aerosol generating article is inserted into the first body; and
a sensor configured to detect deformation of the one end of the aerosol generating article,
wherein the sensor comprises:
an emission portion configured to emit light or ultrasonic waves toward the one end of the aerosol generating article; and
a detection portion configured to receive light or ultrasonic waves reflected from the one end of the aerosol generating article after being emitted from the emission portion.

* * * * *